United States Patent

Shioguchi et al.

[11] Patent Number: 5,990,180
[45] Date of Patent: *Nov. 23, 1999

[54] AQUEOUS COMPOSITION CONTAINING SOLUBILIZED OR DISPERSED OIL-SOLUBLE SUBSTANCE

[75] Inventors: Kaoru Shioguchi; Akifumi Yuki, both of Kanagawa, Japan

[73] Assignee: Mitsubishi Chemical Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/623,958

[22] Filed: Mar. 29, 1996

[30] Foreign Application Priority Data

Mar. 29, 1995 [JP] Japan ..................................... 7-072010

[51] Int. Cl.$^6$ ............................. A23L 1/035; B01F 17/34; B01J 13/00
[52] U.S. Cl. ............................. 516/73; 426/651; 426/654; 514/975; 516/75
[58] Field of Search .................................... 252/312, 356; 426/651, 654; 516/73, 75; 514/975

[56] References Cited

U.S. PATENT DOCUMENTS

| | | | |
|---|---|---|---|
| 2,583,576 | 1/1952 | Kern et al. | 252/312 X |
| 2,628,930 | 2/1953 | Zentner | 252/356 X |
| 3,253,992 | 5/1966 | Brooks | 252/356 X |
| 3,637,774 | 1/1972 | Babayan et al. | . |
| 3,936,391 | 2/1976 | Gabby et al. | 252/356 |
| 4,093,750 | 6/1978 | Babayan | 426/651 X |
| 4,454,113 | 6/1984 | Hemker | 252/312 X |
| 4,959,233 | 9/1990 | Schou et al. | 426/654 X |
| 5,883,274 | 3/1999 | Shioguchi et al. | 554/227 |

FOREIGN PATENT DOCUMENTS

| | | | |
|---|---|---|---|
| 62-250941 | 10/1987 | Japan | A23L 1/035 |
| 6-36862 | 5/1994 | Japan | B01F 17/42 |

OTHER PUBLICATIONS

Kagaku Daijiten, First Edition, p. 1637, issued by Tokyo Kagaku Dojin, 1989.

*Primary Examiner*—Richard D. Lovering
*Attorney, Agent, or Firm*—Sughrue, Mion, Zinn, Macpeak & Seas, PLLC

[57] ABSTRACT

An aqueous composition which comprises an aqueous medium (component C) and an oil-soluble substance (component B) solubilized or dispersed therein by the action of a solubilizing or dispersing agent (component A), said component A comprising a polyglycerol saturated fatty acid ester which has a cloud point of 20° C. or higher and in which at least 70% by weight of the fatty-acid moieties thereof are derived from a saturated fatty acid having 12 to 14 carbon atoms; and the amount of said component A being from 1 to 10 parts by weight per part by weight of said component B.

13 Claims, No Drawings

AQUEOUS COMPOSITION CONTAINING SOLUBILIZED OR DISPERSED OIL-SOLUBLE SUBSTANCE

FIELD OF THE INVENTION

The present invention relates to a composition comprising an oil-soluble substance solubilized or dispersed in an aqueous medium. More particularly, this invention relates to a composition in which an oil-soluble substance such as colorants, flavoring materials, vitamins, antioxidants, preservatives, bactericides, oils, or fats has been solubilized or dispersed in an aqueous medium.

BACKGROUND OF THE INVENTION

Various kinds of conventional articles which are liquid at ordinary temperature, among cosmetics, deodorants, bath additives, fragrances, deodorizers, foods, medicines, and the like, contain oil-soluble substances, such as colorants, flavoring materials, vitamins, antioxidants, preservatives, bactericides, oils, fats, etc., solubilized or dispersed in an aqueous medium by the action of emulsifying agents. However, these articles have a problem that the oil-soluble substances solubilized or dispersed in an aqueous medium with emulsifying agents separate out from the aqueous medium during preparation of the articles or during storage or transportation thereof after their preparation.

Most of the techniques proposed so far for eliminating such oil/water separation problem are to add polyhydric alcohols, surfactants, or the like as solubilizing or dispersing agents. Some of such techniques have come into practical use. Representative examples of the solubilizing or dispersing agents proposed so far include lecithin and surfactants such as polyoxyethylene sorbitan monooleate (nonionic surfactant), ethylene oxide adducts of hydrogenated castor oil, and sucrose fatty acid esters.

Among the conventional solubilizing or dispersing agents, lecithin is extensively used because it is a highly safe substance derived from a natural substance such as egg yolk or soybean. However, since lecithin has insufficient hydrophilicity, use of lecithin for the solubilization or dispersion of oil-soluble substances in aqueous mediums necessitates use of water-soluble solvents, e.g., polyhydric alcohols. If the final product is a food, the additional use of such water-soluble solvents causes problems concerning taste. Another disadvantage of lecithin is that, since it is derived from a natural substance, it is susceptible to putrefaction, rancidity, or the like and thus lacks stability.

Polyoxyethylene-based nonionic surfactants have a disadvantage that the ethylene oxide chain contained as a hydrophilic group in the molecular chain thereof degrades with the lapse of time, resulting in reduced solubilizing or dispersing power. In addition, there is a fear that the degradation of those surfactants may result in formation of formalin, which is a decomposition product of ethylene oxide chain, or in a decrease in pH. Therefore, use of the polyoxyethylene-based nonionic surfactants as food additives is prohibited in Japan from the standpoint of safety. Thus, those surfactants are restricted in their applications. Sucrose fatty acid esters may degrade under acidic conditions, so that they have a problem that they cannot exhibit sufficient solubilizing or dispersing power under low-pH conditions.

On the other hand, solubilizing or dispersing agents comprising polyglycerol fatty acid ester (hereinafter often referred to as PoGE), which are emulsifying agents whose use as a food additive has been authorized, have been proposed (JP-A-61-234920 and JP-A-62-250941). (The term "JP-A" as used herein means an "unexamined published Japanese patent application.") However, use of the proposed solubilizing or dispersing agents comprising PoGE for the solubilization or dispersion of oil-soluble substances in aqueous mediums disadvantageously necessitates additional use of another additive such as polyhydric alcohols. Further, the fatty acid moieties of the PoGE are mainly derived from an unsaturated fatty acid having low long-term stability. Thus, the proposed PoGE-based solubilizing or dispersing agents have problems that taste is influenced by the additives when the article is a food or the like, and that the poor long-term stability influences the distribution and storage of the article.

In addition, use of the conventional solubilizing or dispersing agents in the solubilization or dispersion of oil-soluble substances has disadvantages concerning article production. For example, for solubilizing or dispersing oil-soluble substances in aqueous mediums without fail, it is necessary to employ emulsifiers, high-pressure homogenizers, or the like for the solubilizing or dispersing operation to apply a powerful shearing force to a raw-material mixture. Consequently, there has been a desire for the development of solubilization or dispersion systems which comprise aqueous mediums and oil-soluble substances easily solubilized or dispersed therein, and which are stable over a prolonged period of time and do not influence taste, etc. in food applications.

SUMMARY OF THE INVENTION

An object of the present invention is to accomplish the following conventional subjects.

1. To provide a composition which comprises an oil-soluble substance solubilized or dispersed in an aqueous medium and which can be prepared even when the kinds of additives are reduced and even without the use of an apparatus providing a high-shear, such as emulsifiers or high-pressure homogenizers.

2. To enable the composition comprising a solubilized-or dispersed oil-soluble substance to be stable over a prolonged period of time.

3. For use in a food application, to enable the composition comprising a solubilized or dispersed oil-soluble substance to be stable over a prolonged period of time even when it does not contain an additive such as polyhydric alcohols, which influence taste.

To accomplish the subjects described above, the present invention provides an aqueous composition which, as described in claim 1, comprises an aqueous medium (hereinafter referred to as component C) and an oil-soluble substance (hereinafter referred to as component B) solubilized or dispersed therein by the action of a solubilizing or dispersing agent (hereinafter referred to as component A), said component A comprising polyglycerol saturated fatty acid ester which has a cloud point of 20° C. or higher and in which at least 70% by weight of the fatty-acid moieties thereof are derived from a saturated fatty acid having 12 to 14 carbon atoms; and the amount of said component A being from 1 to 10 parts by weight per part by weight of said component B.

DETAILED DESCRIPTION OF THE INVENTION

The present invention is explained below in detail.

The solubilizing or dispersing agent (component A) in the present invention is used for the purpose of solubilizing or dispersing the oil-soluble substance (component B) in the aqueous medium (component C). It is essential that component A should comprise polyglycerol saturated fatty acid ester which has a cloud point of 20° C. or higher and in which at least 70% by weight of the fatty-acid moieties are derived from a saturated fatty acid having 12 to 14 carbon atoms.

In the present invention, the term "solubilized or dispersed" used means that the aqueous medium (component C) and the oil-soluble substance (component B) therein are in a homogeneous state, such as the state in which component B has been thermodynamically stably solubilized in component C, the state of a microemulsion, or the state of an emulsion of the W/O or O/W type, etc.

The individual components are explained below in detail.

Component B:

Component B is the substance which itself is oil-soluble and substantially water-insoluble, and is solubilized or dispersed in the aqueous medium by the action of component A, which will be described below, to give a final product. Component B is not particularly limited as long as it has the properties described above. Examples thereof include colorants, flavoring materials, vitamins, antioxidants, preservatives, bactericides, oils, and fats.

Examples of the colorant include β-carotene, annatto pigment, and turmeric pigment. Examples of the flavoring material include orange oil and menthol. Examples of the vitamin include vitamin A, vitamin B, and vitamin E. Examples of the antioxidant include tocopherols, ascorbyl stearate, and γ-oryzanol. Examples of the preservative and bactericide include dehydroacetic acid. Examples of the oil and fat include triglyceride of 2-ethylhexanoic acid, various animal oils, and various vegetable fats and oils.

Component A:

Component A serves to solubilize or disperse component B in the aqueous medium, and comprises polyglycerol saturated fatty acid ester (PoGE) which satisfies the requirements specified hereinabove. The polyglycerol moiety of this PoGE may have a degree of polymerization of 4 or higher, preferably from 4 to 12 in usual cases. From the standpoint of safety of the PoGE as additives, the degree of polymerization thereof is preferably from 6 to 12, more preferably from 10 to 12. The term "degree of polymerization" used in this specification means the number average degree of polymerization.

In producing the PoGE, the fatty acid and the polyglycerol (hereinafter referred to as PoG) may be reacted in such a proportion that the molar ratio of the fatty acid to the hydroxyl groups of the PoG is in the range of from 1:6 to 1:100.

Experiments performed by the present inventors revealed that at least 70% by weight of the fatty-acid moieties contained in the PoGE should be derived from the saturated fatty acid having 12 to 14 carbon atoms. The reasons are as follows. If the fatty-acid moieties contained in the PoGE are derived from fatty acid having less than 12 carbon atoms, this undesirably results in a decrease in solubilizing or dispersing power or, in the case of use as additives for foods (e.g., beverages), impair flavor or taste. On the other hand, if the fatty-acid moieties are derived from fatty acid having more than 14 carbon atoms, it is difficult to prepare a stable solubilization or dispersion system when solubilization or dispersion is conducted under acidic conditions with a pH of 3 or lower, and the solubilization or dispersion system prepared under such acidic conditions may undesirably generate precipitate, etc. If the fatty-acid moieties derived from saturated fatty acid are less than 70% by weight based on the total weight of the fatty-acid moieties, this undesirably results in impaired flavor or taste during long-term storage. Examples of the saturated fatty acid having 12 to 14 carbon atoms include lauric acid and myristic acid. Such saturated fatty acids may be used alone or as a mixture of two or more.

The proportion of the moieties derived from saturated fatty acid having 12 to 14 carbon atoms in all fatty-acid moieties contained in the PoGE is desirably 80% by weight or higher, preferably 90% by weight or higher.

The kind of fatty-acid moieties may be determined by selecting fatty acids for use as a starting material in producing the PoGE so that the number of carbon atoms contained therein, the proportion of saturated fatty acid, etc. are within the respective ranges specified above.

Experiments performed by the present inventors further revealed that if the cloud point of PoGE as determined in 10% (by weight based on the total weight of the aqueous sodium sulfate solution) aqueous sodium sulfate solution is below 20° C., it is difficult to stably solubilize or disperse the oil-soluble substance and the composition prepared may undergo separation of the oil-soluble substance, generation of precipitate, etc.

In the present invention, the cloud point of a PoGE is determined by the method described below. A 10% (by weight based on the total weight of the aqueous sodium sulfate solution) aqueous sodium sulfate solution was prepared. Then, PoGE was mixed in such an amount as to result in a PoGE concentration of 1% by weight based on the total weight of the solution. This mixture was placed in a glass tube, which was then sealed and heated to homogenize the contents. This glass tube was immersed for several minutes to 1 hour in a thermostatic bath regulated so as to have a given temperature, and the liquid in the glass tube was visually examined for phase separation. The above procedure was repeated at various temperatures of the thermostatic bath by elevating the temperature at given intervals. The temperature at which the oil-soluble component first separated out was taken as cloud point.

The PoGE having the properties described above can be produced by introducing a saturated fatty acid having 12 to 14 carbon atoms and a PoG into a reactor and reacting the reactants at a pressure of from ordinary pressure to several atm. and a temperature of from 150 to 300° C. in the presence of a catalyst. Examples of usable catalysts include alkalis such as potassium hydroxide and sodium hydroxide. The use amount thereof may be suitably selected in the range of from 0.001 to 0.025% by weight based on the total amount of the reactants.

The cloud point of the PoGE can be easily regulated by selecting reaction conditions used for the synthesis thereof. For example, when a cloud point is lower than 20° C., examples of the method for raising the cloud point include the following three methods: (1) decreasing the molar proportion of the fatty acid to the PoG; (2) increasing the amount of the alkali catalyst (Reason: the alkali catalyst used in PoGE production reacts with the fatty acid as a starting material to yield a fatty acid alkali salt (soap) and this by-product tends to elevate the cloud point); and (3) increasing the average degree of polymerization of the starting material PoG; or the like.

Component C:

Component C is water and functions as the medium in which the oil-soluble substance (component B) is solubilized or dispersed. This water is preferably one obtained by subjecting industrial water to ion-exchange treatment to remove cations and anions therefrom.

The composition of the present invention, which comprises the oil-soluble substance (component B) solubilized or dispersed in the aqueous medium (component C), can be easily prepared by a process in which a given amount of the above-described solubilizing or dispersing agent (component A) and a given amount of component B are mixed together with stirring and heating and this mixture is added to the aqueous medium (component C) to solubilize or disperse the oil-soluble substance, following by cooling the resulting solution or dispersion to room temperature. In this process, powerful mechanical agitation as in conventional processes is not essential, and moderate stirring such as, e.g., stirring by shaking is sufficient. It should however be noted that use of stirring for applying a high shearing force is not excluded from this invention.

According to experiments performed by the present inventors, the amount of the solubilizing or dispersing agent (component A) can be selected in the range of from 1 to 10 parts by weight per part by weight of the oil-soluble substance (component B), although it varies depending on the kind of component B. Amounts of component A smaller than 1 part by weight are undesirable in that it is difficult to solubilize or disperse component B. Amounts thereof exceeding 10 parts by weight are undesirable in that even when the addition amount of component A is increased, its effect is not enhanced in proportion thereto. The incorporation of 1 part by weight or more of component A is preferred especially when the composition has a pH lower than 3, because such component A amount enables the object of the present invention to be accomplished effectively. If the amount of component A is smaller than 1 part by weight per part by weight of component B in preparing a composition having a pH lower than 3, the operation for solubilizing or dispersing an oil-soluble substance only results in an unstable solubilization or dispersion system which suffers separation of the oil-soluble substance (component B). Thus, especially under acidic conditions, too small amounts of component A result in troubles such as the formation of a precipitate to make it impossible to obtain a composition comprising an oil-soluble substance stably solubilized or dispersed in an aqueous medium.

The composition of the present invention contains a solubilized or dispersed oil-soluble substance (component B) in any desired proportion, which is stable not only under neutral conditions, but also under acidic conditions with a pH of 2 to 5 by regulating the amount of component A. Thus, solubilized or dispersed composition which does not cause separation or precipitation of component B can be obtained. Although acidic foods generally have a pH of 3.3 or higher, the composition of the present invention is stable at such pH or below.

The content of component B in the whole composition is desirably from 10 to 10,000 ppm, preferably from 100 to 5,000 ppm, because the composition having such an component B content is stable even at a low pH of 5 or lower.

Besides the essential components A and B mixed with an aqueous medium as component C, other components may be added/compounded into the composition of the present invention if desired and necessary. Such optional components, which are selected according to the use of the composition, include water-soluble additives, e.g., saccharides and polyhydric alcohols, and pH regulators. Specific examples of the water-soluble additives include propylene glycol, glycerol, sorbitol, xylitol, arabitol, maltitol, lactitol, sorbitan, xylose, arabinose, mannose, lactose, sugar, coupling sugar, glucose, high maltose syrups, acid-converted syrups, malt syrups, maltose, isomerized sugars, fructose, maltitol, hydrogenated glucose syrups, and honey. Examples of the pH regulators include citric acid. These additives may be used alone or in combination of two or more thereof.

The incorporation amount of those optional components in the whole composition may be suitably selected according to the use of the product (cf. *Shiteihinmoku Shokuhintenkabutsubinran*, 1993 (Shokuhintokagakusha)).

The composition of the present invention is usable in various applications which are liquid at ordinary temperature, such as cosmetics, deodorants, bath additives, fragrances, deodorizers, foods, and medicines. These products suffer neither separation of the oil-soluble substance nor formation of a precipitate even under acidic conditions, since the oil-soluble substance has been stably solubilized or dispersed in the aqueous medium.

The present invention brings about the following especially advantageous effects, and has an extremely high industrial value.

1. The composition of the present invention can be easily prepared, because in solubilizing or dispersing an oil-soluble substance in an aqueous medium, there is no need of using a high-shear apparatus such as an emulsifier or high-pressure homogenizer even when the kinds of additives are reduced.

2. The composition of the present invention is stable over a prolonged period of time and never denatures during storage or distribution.

3. The composition of the present invention never impairs the taste, flavor, and other properties of foods, e.g., beverages, medicines, cosmetics, etc.

The present invention will be explained below in more detail by reference to Production Examples and Examples, but the invention should not be construed as being limited thereto unless the spirit thereof is departed from.

Unless otherwise indicated, all parts, ratios, percents, and the like are by weight.

In the following Production Examples, the cloud point of each reaction product was measured by the following method. The raw materials used in the following Production Examples, Examples, and Comparative Examples are as follows.

Method for Measuring Cloud Point of Reaction Product

A 10% (by weight based on the total weight of the aqueous sodium sulfate solution) aqueous sodium sulfate solution was prepared. Then, the reaction product obtained in each Production Example was mixed in such an amount as to result in the concentration of 1% by weight based on the total weight of the solution. This mixture was placed in a glass tube, which was then sealed and heated to homogenize the contents. This glass tube was immersed for 30 minutes in a thermostatic bath regulated so as to have a given temperature, and the liquid in the glass tube was visually examined for phase separation. The above procedure was repeated at various temperatures of the thermostatic bath by elevating the temperature at 5° C. intervals. The temperature at which the oil-soluble component first separated out was taken as cloud point.

Raw Materials Used

Polyglycerol: Polyglycerol #750 (manufactured by Sakamoto Yakuhin Kogyo Co., Ltd., Japan; hydroxyl value, 890; average degree of polymerization, 11)

Lauric acid: Sunfat #12 (manufactured by Lion Corp., Japan; purity, 95% or higher)

Myristic acid: Sunfat #12 (manufactured by Lion Corp.; purity, 95% or higher)

Palmitic acid: Lunac P-95 (manufactured by Kao Corp., Japan; purity, 95% or higher)

Stearic acid: Stearin 750 (manufactured by Nippon Oil & Fats Co., Ltd., Japan; 75 wt % stearic acid, 25 wt % palmitic acid)

PRODUCTION EXAMPLE 1

(Production of PoGE-A to -C)

Into a 2-liter reactor equipped with a stirrer, thermometer, heating jacket, gas-introducing opening, and starting material-feeding opening was first introduced 1,200 g of polyglycerol (PoG). Into this reactor were then introduced lauric acid and 10% aqueous sodium hydroxide solution. The amount of the lauric acid introduced was changed so as to result in the lauric acid/PoG molar ratios shown in Table 1. The amount of the sodium hydroxide was 0.0025% by weight based on the total amount of the PoG and the lauric acid.

In a nitrogen stream at ordinary pressure, the inner temperature was elevated to 240° C. and allowed to react at this temperature for 2.5 hours, and were then further heated to 260° C. and allowed to react at this temperature for 4 hours. After completion of the reaction, the contents were cooled to room temperature. Thus, liquid polyglycerol lauric acid esters (PoGE-A to -C) were obtained.

The reaction products obtained were examined for cloud point by the method described above. The results obtained are shown in Table 1.

TABLE 1

| PoGE abbreviation | Lauric acid/PoG molar ratio | Cloud point |
| --- | --- | --- |
| PoGE-A | 0.7 | ≧90° C. |
| PoGE-B | 1.0 | 70° C. |
| PoGE-C | 1.5 | 10° C. |

PRODUCTION EXAMPLE 2

(Production of PoGE-D)

Into the reactor used in Production Example 1 was first introduced 1,200 g of PoG. Into this reactor were then introduced myristic acid (in such an amount as to result in a myristic acid/PoG molar ratio of 1) and 10% aqueous sodium hydroxide solution (in such an amount as to result in a sodium hydroxide amount of 0.0025% by weight based on the total amount of the reactants).

Reaction was conducted under the same conditions as in Production Example 1 to obtain polyglycerol myristic acid ester. This reaction product was dispersed in an about 5-fold (by weight) amount of acetone. The resulting dispersion was heated and then decanted to separate the reaction product into a soluble part and an insoluble part. The insoluble matter was vacuum-dried. This acetone-insoluble matter is referred to as PoGE-D.

The cloud point of this insoluble matter was measured, and was found to be 90° C. or higher.

PRODUCTION EXAMPLE 3

(Production of PoGE-E and PoGE-F)

Into the reactor used in Production Example 1 was first introduced 1,200 g of PoG. Into this reactor were then introduced palmitic acid or stearic acid (in such an amount that the molar ratio of palmitic acid or stearic acid to PoG was shown in Table 2) and 10% aqueous sodium hydroxide solution (in the same amount as the above).

Reaction was conducted under the same conditions as in Production Example 1 to obtain polyglycerol palmitic acid ester (hereinafter referred to as PoGE-E) or polyglycerol stearic acid ester (hereinafter referred to as PoGE-F).

The reaction products obtained were examined for cloud point by the method described above. The results obtained are shown in Table 2.

TABLE 2

| PoGE abbreviation | Kind of fatty acid | Fatty acid/PoG molar ratio | Cloud point |
| --- | --- | --- | --- |
| POGE-E | palmitic acid | 0.7 | ≧30 ° C. |
| POGE-F | stearic acid | 1.0 | ≧30 ° C. |

EXAMPLE 1

Twenty-five parts by weight of D,L-α-tocopherol (vitamin E) (manufactured by Tokyo Kasei Kogyo Co., Ltd., Japan; special grade) as an oil-soluble substance and 75 parts by weight of PoGE-A produced in Production Example 1 were weighed out (component B/component A=⅓). The two components were mixed with each other and stirred at 60 to 70° C. to obtain a mixture.

A 0.2 g portion of this mixture was mixed and stirred with 100 ml of 25° C. water regulated with citric acid so as to have a pH of 3. As a result, a composition in which the oil-soluble substance had been homogeneously solubilized or dispersed was obtained. Even when this composition was allowed to stand at 25° C. for 1 month and then at 5° C. for 1 month, neither oil/water separation nor precipitation occurred.

EXAMPLE 2

Fifteen parts by weight of vitamin E (the same kind as in Example 1) and 85 parts by weight of PoGE-A were weighed out (component B/component A=⅕.₇), and mixed with each other and stirred at 60 to 70° C. to obtain a mixture.

Subsequently, 0.07 g, 0.13 g, 0.33 g, 0.67 g, and 1.33 g portions of this mixture were weighed out, and each was mixed and stirred with 100 ml of 25° C. water regulated with citric acid so as to have a pH of 3. The compositions thus obtained were all homogeneous compositions in which the oil-soluble substance had been homogeneously solubilized or dispersed. Even when these compositions were allowed to stand at 25° C. for. 1 month and then at 5° C. for 1 month, neither oil/water separation nor precipitation occurred.

EXAMPLE 3

Twenty parts by weight of vitamin E (the same kind as in Example 1) and 80 parts by weight of PoGE-B were weighed out (component B/component A=¼), and mixed with each other and stirred at 60 to 70° C. to obtain a mixture.

A 0.25 g portion of this mixture was mixed and stirred with 100 ml of 25° C. water regulated with citric acid so as to have a pH of 3. As a result, a composition in which the oil-soluble substance had been homogeneously solubilized or dispersed was obtained. Even when this composition was allowed to stand at 25° C. for 1 month and then at 5° C. for 1 month, neither oil/water separation nor precipitation occurred.

EXAMPLE 4

Twenty parts by weight of vitamin E (the same kind as in Example 1) and 80 parts by weight of PoGE-D were weighed out (component B/component A=¼), and mixed with each other and stirred at 60 to 70° C. to obtain a mixture.

A 0.25 g portion of this mixture was mixed and stirred with 100 ml of 25° C. water regulated with citric acid so as

EXAMPLE 5

Fifteen parts by weight of orange oil (manufactured by Kyowa Koryo Kagaku K. K., Japan) as an oil-soluble substance and 85 parts by weight of PoGE-A were weighed out (component B/component A=$1/5.7$), and mixed with each other and stirred at 60 to 70° C. to obtain a mixture.

A 0.33 g portion of this mixture was mixed and stirred with 100 ml of 25° C. water regulated with citric acid so as to have a pH of 3. As a result, a composition in which the oil-soluble substance had been homogeneously solubilized or dispersed was obtained. Even when this composition was allowed to stand at 25° C. for 1 month, neither oil/water separation nor precipitation occurred.

EXAMPLE 6

Ten parts by weight of 2-ethylhexanoic acid triglyceride (manufactured by The Nisshin Oil Mills, Ltd., Japan) as an oil-soluble substance and 90 parts by weight of PoGE-A were weighed out (component B/component A=$1/9$), and mixed with each other and stirred at 60 to 70° C. to obtain a mixture.

A 0.50 g portion of this mixture was mixed and stirred with 100 ml of 25° C. water regulated with citric acid so as to have a pH of 3. As a result, a composition in which the oil-soluble substance had been homogeneously solubilized or dispersed was obtained. Even when this composition was allowed to stand at 25° C. for 1 month and then at 5° C. for 1 month, neither oil/water separation nor precipitation occurred.

EXAMPLE 7

Ten parts by weight of 2-ethylhexanoic acid triglyceride (the same kind as in Example 6) and 90 parts by weight of PoGE-B were weighed out (component B/component A=$1/9$), and mixed with each other and stirred at 60 to 70° C. to obtain a mixture.

A 0.50 g portion of this mixture was mixed and stirred with 100 ml of 25° C. water regulated with citric acid so as to have a pH of 3. As a result, a composition in which the oil-soluble substance had been homogeneously solubilized or dispersed was obtained. Even when this composition was allowed to stand at 25° C. for 1 month, neither oil/water separation nor precipitation occurred.

EXAMPLE 8

Ten parts by weight of vitamin E (the same kind as in Example 1) and 60 parts by weight of PoGE-A were weighed out (component B/component A=$1/6$). These components were mixed and stirred with 30 parts by weight of special-grade glycerol (manufactured by Kishida Chemical Co., Ltd., Japan) at 60 to 70° C. to obtain a mixture.

A 0.50 g portion of this mixture was mixed and stirred with 100 ml of 25° C. water regulated with citric acid so as to have a pH of 3. As a result, a composition in which the oil-soluble substance had been homogeneously solubilized or dispersed was obtained. Even when this composition was allowed to stand at 25° C. for 1 month and then at 5° C. for 1 month, neither oil/water separation nor precipitation occurred.

EXAMPLE 9

Seven parts by weight of vitamin A palmitate (manufactured by Riken Vitamin Co., Ltd., Japan) as an oil-soluble substance and 63 parts by weight of PoGE-B were weighed out (component B/component A=$1/9$). These components were mixed and stirred with 30 parts by weight of special-grade glycerol (the same kind as in Example 8) at 60 to 70° C. to obtain a mixture.

A 0.14 g portion of this mixture was mixed and stirred with 100 ml of 25° C. water regulated with citric acid so as to have a pH of 3. As a result, a composition in which the oil-soluble substance had been homogeneously solubilized or dispersed was obtained. Even when this composition was allowed to stand at 25° C. for 1 month, neither oil/water separation nor precipitation occurred.

EXAMPLE 10

Forty parts by weight of vitamin E (the same kind as in Example 1) and 80 parts by weight of PoGE-B were weighed out (component B/component A=$1/2$), and mixed with each other and stirred at 60 to 70° C. to obtain a mixture.

A 0.15 g portion of this mixture was mixed and stirred with 100 ml of 25° C. water regulated with citric acid so as to have a pH of 4. As a result, a composition in which the oil-soluble substance had been homogeneously solubilized or dispersed was obtained. Even when this composition was allowed to stand at 25° C. for 1 month and then at 5° C. for 1 month, neither oil/water separation nor precipitation occurred.

EXAMPLE 11

Thirty parts by weight of 2-ethylhexanoic acid triglyceride (the same kind as in Example 6) and 45 parts by weight of PoGE-B were weighed out (component B/component A=$1/1.5$), and mixed with each other and stirred at 60 to 70° C. to obtain a mixture.

A 0.13 g portion of this mixture was mixed and stirred with 100 ml of 25° C. water regulated with citric acid so as to have a pH of 5. As a result, a composition in which the oil-soluble substance had been homogeneously solubilized or dispersed was obtained. Even when this composition was allowed to stand at 25° C. for 1 month and then at 5° C. for 1 month, neither oil/water separation nor precipitation occurred.

COMPARATIVE EXAMPLE 1

Ten parts by weight of vitamin E (the same kind as in Example 1) and 90 parts by weight of PoGE-C (having a cloud point of 10° C.) were weighed out (component B/component A=$1/9$), and mixed with each other and stirred at 60 to 70° C. to obtain a mixture.

A 0.5 g portion of this mixture was mixed and stirred with 100 ml of 25° C. water regulated with citric acid so as to have a pH of 3. As a result, precipitation occurred, and a composition in which an oil-soluble substance had been homogeneously solubilized or dispersed could not be obtained.

COMPARATIVE EXAMPLE 2

Fifteen parts by weight of vitamin E (of the same kind as in Example 1) and 85 parts by weight of PoGE-E (in which the fatty-acid moieties were derived from palmitic acid) were weighed out (component B/component A=$1/5.7$), and mixed with each other and stirred at 60 to 70° C. to obtain a mixture.

A 0.33 g portion of this mixture was mixed and stirred with 100 ml of 25° C. water regulated with citric acid so as to have a pH of 3. As a result, precipitation occurred, and a composition in which an oil-soluble substance had been homogeneously solubilized or dispersed could not be obtained.

COMPARATIVE EXAMPLE 3

Twenty parts by weight of vitamin E (the same kind as in Example 1) and 80 parts by weight of PoGE-F (in which the fatty-acid moieties were derived from stearic acid) were weighed out (component B/component A=¼), and mixed with each other and stirred at 60 to 70° C. to obtain a mixture.

A 0.25 g portion of this mixture was mixed and stirred with 100 ml of 25° C. water regulated with citric acid so as to have a pH of 3. As a result, precipitation occurred, and a composition in which an oil-soluble substance had been homogeneously solubilized or dispersed could not be obtained.

TABLE 3

| Item No. | Kind of POGE | Component B/ Component A ratio (by weight) | Additive | State of Composition |
|---|---|---|---|---|
| Example 1 | PoGE-A | 1/3 | — | solution or dispersion |
| Example 2 | PoGE-A | 1/5.7 | — | solution or dispersion |
| Example 3 | PoGE-B | 1/4 | — | solution or dispersion |
| Example 4 | PoGE-D | 1/4 | — | solution or dispersion |
| Example 5 | PoGE-A | 1/5.7 | — | solution or dispersion |
| Example 6 | PoGE-A | 1/9 | — | solution or dispersion |
| Example 7 | PoGE-B | 1/9 | — | solution or dispersion |
| Example 8 | PoGE-A | 1/6 | glycerol | solution or dispersion |
| Example 9 | PoGE-B | 1/9 | glycerol | solution or dispersion |
| Example 10 | PoGE-B | 1/2 | — | solution or dispersion |
| Example 11 | PoGE-B | 1/1.5 | — | solution or dispersion |
| Comarative Example 1 | PoGE-C | 1/9 | — | precipitation occurred |
| Comparative Example 2 | PoGE-E | 1/5.7 | — | precipitation occurred |
| Comparative Example 3 | PoGE-F | 1/4 | — | precipitation occurred |

The results of Examples 1 to 11 and Comparative Examples 1 to 3 show the following.

(1) The compositions according to the present invention, in which the oil-soluble substance had been homogeneously solubilized or dispersed, were all homogeneous solution or dispersion systems which were stable and suffered neither oil/water separation nor precipitation even in long-term standing (see Examples 1 to 11).

(2) In contrast, in the case of using a PoGE which did not satisfy the requirement regarding cloud point as specified in claim 1, precipitation occurred in the composition and a homogeneous solution or dispersion system was not formed (see Comparative Example 1).

(3) Further, in the case of using PoGE which did not satisfy the requirement as specified in claim 1 regarding the fatty-acid moieties contained therein, precipitation occurred in the compositions and a homogeneous solution or dispersion system was not formed (see Comparative Examples 2 and 3).

While the invention has been described in detail and with reference to specific embodiments thereof, it will be apparent to one skilled in the art that various changes and modifications can be made therein without departing from the spirit and scope thereof.

What is claimed is:

1. An aqueous composition comprising an aqueous medium and an oil-soluble substance solubilized or dispersed therein by the action of a solubilizing or dispersing agent, said solubilizing or dispersing agent comprising a polyglycerol saturated fatty acid ester which has a cloud point of 20° C. or higher and in which at least 70% by weight of the fatty acid moieties thereof are derived from a saturated fatty acid having 12 to 14 carbon atoms; and the amount of said solubilizing or dispersing agent being from 1 to 10 parts by weight per part by weight of said oil-soluble substance, wherein the cloud point of the polyglycerol saturated fatty acid ester is determined at a concentration of 1% by weight of the polyglycerol saturated fatty acid ester in a 10% by weight aqueous sodium sulfate solution.

2. The composition as claimed in claim 1, wherein the polyglycerol moiety of said polyglycerol saturated fatty acid ester has a degree of polymerization of 4 or higher.

3. The composition as claimed in claim 1, wherein the polyglycerol moiety of said polyglycerol saturated fatty acid ester has a degree of polymerization of from 4 to 12.

4. The composition as claimed in claim 1, wherein the polyglycerol moiety of said polyglycerol saturated fatty acid ester has a degree of polymerization of from 6 to 12.

5. The composition as claimed in claim 1, wherein the polyglycerol moiety of said polyglycerol saturated fatty acid ester has a degree of polymerization of from 10 to 12.

6. The composition as claimed in claim 1, wherein said saturated fatty acid is at least one member selected from the group consisting of lauric acid and myristic acid.

7. The composition as claimed in claim 1, wherein at least 80% by weight of said fatty-acid moieties are derived from a fatty acid having 12 to 14 carbon atoms.

8. The composition as claimed in claim 1, wherein at least 90% by weight of said fatty-acid moieties are derived from a fatty acid having 12 to 14 carbon atoms.

9. The composition as claimed in claim 1, which has a pH of 5 or lower.

10. The composition as claimed in claim 1, which has a pH of from 2 to 5.

11. The composition as claimed in claim 1, wherein the content of said oil-soluble substance is from 10 to 10,000 ppm based on the whole composition.

12. The composition as claimed in claim 1, wherein the content of said oil-soluble substance is from 100 to 5,000 ppm based on the whole composition.

13. The composition as claimed in claim 1, which has a cloud point of 90° C. or higher.

* * * * *